(12) United States Patent
Bogdan et al.

(10) Patent No.: US 9,162,214 B2
(45) Date of Patent: Oct. 20, 2015

(54) SUBSTANTIALLY NONPOROUS SUBSTRATE SUPPORTED NOBLE METAL- AND LANTHANIDE-CONTAINING CATALYSTS FOR HYDROGENATION REACTIONS

(71) Applicant: UOP LLC, Des Plaines, IL (US)

(72) Inventors: Paula L. Bogdan, Mount Prospect, IL (US); Valeria J. Nemeth, Las Vegas, NV (US); Simon R. Bare, Naperville, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 14/463,155

(22) Filed: Aug. 19, 2014

(65) Prior Publication Data

US 2014/0357911 A1    Dec. 4, 2014

Related U.S. Application Data

(62) Division of application No. 13/108,206, filed on May 16, 2011, now Pat. No. 8,822,370.

(51) Int. Cl.
| | | |
|---|---|---|
| *C07C 5/02* | (2006.01) | |
| *C07C 5/03* | (2006.01) | |
| *C07C 5/10* | (2006.01) | |
| *B01J 21/00* | (2006.01) | |

(Continued)

(52) U.S. Cl.
CPC *B01J 23/63* (2013.01); *B01J 23/44* (2013.01); *B01J 35/06* (2013.01); *B01J 35/1009* (2013.01); *B01J 37/0207* (2013.01); *B01J 37/18* (2013.01); *C07C 5/03* (2013.01); *C07C 2101/14* (2013.01); *C07C 2523/10* (2013.01); *C07C 2523/44* (2013.01); *C07C 2529/068* (2013.01)

(58) Field of Classification Search
CPC .. C07C 5/03; C07C 2523/10; C07C 2523/38; C07C 2523/44; C07C 2523/63; B01J 23/10; B01J 23/38; B01J 23/44; B01J 23/63; B01J 21/00
USPC ......... 502/252, 261–263, 302, 327, 328, 330, 502/333, 339, 439; 585/269, 277
See application file for complete search history.

(56) References Cited

U.S. PATENT DOCUMENTS 3,751,497 A  *  8/1973  Schwerdtel et al. .......... 585/273
4,440,631 A  *  4/1984  Togari et al. ................. 208/112

(Continued)

FOREIGN PATENT DOCUMENTS

| CA | 2718882 A1 | 9/2010 |
|---|---|---|
| WO | 2008060989 A2 | 5/2008 |

OTHER PUBLICATIONS

Search Report dated Jan. 19, 2015 for corresponding European Appl. No. 12786282.

(Continued)

*Primary Examiner* — Cam N. Nguyen

(57) ABSTRACT

Aspects of the invention relate to hydrogenation catalysts, and hydrogenation processes using these catalysts, having particular characteristics, in terms of the amount and type of metal hydrogenation component (or catalytic constituent), as well as the support or substrate. The catalyst compositions, comprising both a noble metal and a lanthanide element on a substantially non-porous substrate, provide advantageous performance characteristics, including conversion, selectivity, and activity stability, as demanded in industrial hydrogenation and selective hydrogenation applications.

20 Claims, 3 Drawing Sheets

(51) Int. Cl.
  *B01J 23/00* (2006.01)
  *B01J 23/40* (2006.01)
  *B01J 23/42* (2006.01)
  *B01J 23/44* (2006.01)
  *B01J 23/58* (2006.01)
  *B01J 23/02* (2006.01)
  *B01J 21/04* (2006.01)
  *B01J 23/63* (2006.01)
  *B01J 37/18* (2006.01)
  *B01J 35/06* (2006.01)
  *B01J 35/10* (2006.01)
  *B01J 37/02* (2006.01)

(56) References Cited

U.S. PATENT DOCUMENTS

| | | | | |
|---|---|---|---|---|
| 5,051,392 | A * | 9/1991 | Mabilon et al. | 502/303 |
| 6,096,933 | A * | 8/2000 | Cheung et al. | 585/260 |
| 6,197,991 | B1 * | 3/2001 | Spivack et al. | 558/274 |
| 6,201,146 | B1 * | 3/2001 | Spivack et al. | 558/274 |
| 6,355,597 | B1 * | 3/2002 | Spivack et al. | 502/353 |
| 6,380,417 | B1 * | 4/2002 | Spivack et al. | 558/274 |
| 6,514,900 | B2 * | 2/2003 | Spivack et al. | 502/224 |
| 6,566,299 | B1 * | 5/2003 | Spivack et al. | 502/302 |
| 6,858,769 | B2 * | 2/2005 | Woodle et al. | 585/658 |
| 7,030,055 | B2 * | 4/2006 | Yaluris et al. | 502/326 |
| 7,453,017 | B2 * | 11/2008 | Moon et al. | 585/277 |
| 7,622,412 | B2 * | 11/2009 | Hill et al. | 502/34 |
| 7,943,104 | B2 * | 5/2011 | Kozlov et al. | 423/213.5 |
| 8,338,654 | B2 * | 12/2012 | Giedigkeit et al. | 585/259 |
| 8,519,207 | B2 * | 8/2013 | Armbruester et al. | 585/259 |
| 2002/0028853 | A1 * | 3/2002 | Manzer et al. | 518/713 |
| 2002/0068843 | A1 * | 6/2002 | Dai et al. | 585/260 |
| 2005/0081443 | A1 * | 4/2005 | Aiello et al. | 48/198.3 |
| 2009/0264277 | A1 * | 10/2009 | Raj et al. | 502/4 |
| 2010/0196255 | A1 * | 8/2010 | Horiuchi et al. | 423/502 |
| 2010/0273645 | A1 * | 10/2010 | Bedard et al. | 502/245 |
| 2011/0172088 | A1 * | 7/2011 | Bedard et al. | 502/204 |
| 2012/0258856 | A1 * | 10/2012 | Horiuchi et al. | 502/302 |
| 2012/0298554 | A1 * | 11/2012 | Negiz et al. | 208/111.01 |

OTHER PUBLICATIONS

Search Report dated Mar. 12, 2015 for corresponding Canadian Appl. No. 2,828,762.

* cited by examiner

SUBSTANTIALLY NONPOROUS SUBSTRATE SUPPORTED NOBLE METAL- AND LANTHANIDE-CONTAINING CATALYSTS FOR HYDROGENATION REACTIONS

CROSS-REFERENCE TO RELATED APPLICATION

This application is a Division of application Ser. No. 13/108,206 filed May 16, 2011, now U.S. Pat. No. 8,822,370 the contents of which are hereby incorporated by reference in its entirety.

FIELD OF THE INVENTION

The present invention relates to catalysts and methods for the hydrogenation of a feedstock comprising a compound having a hydrogenatable site. Representative catalysts comprise a noble metal and a lanthanide element deposited on a support comprising a substantially non-porous substrate.

DESCRIPTION OF RELATED ART

Hydrogenation processes are well established and used throughout the refining, petrochemical, and chemical industries. Hydrogenation refers to a type of chemical reduction in which hydrogen is added to a reactant at a site of unsaturation (a "hydrogenatable" site). In the case of organic compounds (e.g., hydrocarbons, including heteroatom-substituted hydrocarbons), such a site is often a carbon-carbon double bond (e.g., in the case of alkenes), a carbon-carbon triple bond (e.g., in the case of alkynes), or a carbon-heteroatom bond, with typical heteroatoms being oxygen (O), nitrogen (N), or sulfur (S) (e.g., in the case of ketones, carboxylic acids, esters, aldehydes, imines, nitriles, thiones, thiocarboxylic acids, thioesters, or thioaldehydes).

Hydrogenation is conventionally carried out in the presence of a catalyst, in order to activate molecular hydrogen and thereby achieve economically attractive reaction kinetics under favorable conditions of temperature and pressure. For example, the catalytic hydrogenation of benzene, having three carbon-carbon double bonds in the aromatic ring, is practiced commercially to reduce benzene concentrations in gasoline blend stocks (and ultimately the gasoline product itself) to acceptable levels. Processes for catalytic hydrogenation of ketones and aldehydes are useful and in fact indispensable for the synthesis of alcohols as precursors or valuable end products in a number of industries, including pharmaceuticals and agrochemicals. "Selective" hydrogenation processes refer to a subset of hydrogenation processes that are also of significant industrial importance. Examples include the selective hydrogenation of acetylene contaminant in an ethylene-containing feedstock (e.g., obtained as a product of thermal ethane cracking) and the selective hydrogenation of butadiene in a butene-containing feedstock (e.g., obtained as a product of fluid catalytic cracking or butane dehydrogenation). In these examples, therefore, it is desired to selectively hydrogenate a relatively more reactive hydrogenatable site of a compound present in the feedstock (e.g., the hydrogenatable sites in acetylene or butadiene) without hydrogenating a relatively less reactive hydrogenatable site of other compounds of the feedstock, corresponding to the products of selective hydrogenation (e.g., ethylene or butene).

Solid catalysts useful for hydrogenation or selective hydrogenation typically comprise a metal hydrogenation component, often one or more of nickel, platinum, palladium, rhodium, or ruthenium, deposited on a porous support material. Other catalysts, comprising a substantially non-porous support material and useful for a number of catalytic processes including hydrogenation, are described in US 2009/0275788 and US 2010/0273645. Of particular importance in any catalytic hydrogenation process is the degree of conversion of the starting materials and the selectivity of converted products to the desired, hydrogenated product(s). The product of the percent conversion and the percent selectivity, which is namely the percent of the theoretical yield of the desired product(s), should be as high as possible. Other fundamental considerations relate to the activity of the catalyst, based on the level of conversion or reaction rate under a given set of reaction conditions (e.g., temperature, pressure, and residence time or space velocity).

Also having a considerable impact on the overall economics of a given hydrogenation process is the activity stability, which relates to the on-stream operating time over which a catalyst can maintain acceptable performance, in terms of conversion and selectivity. Activity stability may be quantified, for example, according to (i) the loss of activity, for example a measured conversion level, for a given set of reaction conditions over time or otherwise (ii) the rate of increase in the catalyst bed temperature, as required to maintain a given activity, for example a measured conversion level, with all other operating conditions held constant. Activity stability governs the frequency with which a hydrogenation catalyst must be replaced and/or regenerated, and this parameter therefore significantly affects the overall material and operating costs required in catalytic hydrogenation processes. The cost of the catalyst is largely a function of the amount of the metal hydrogenation component used, especially when this component includes one or more noble metals (e.g., palladium), which are generally expensive.

There is a therefore an ongoing need for hydrogenation catalysts and associated, efficient processes for the hydrogenation of organic compounds including alkynes, dienes, and aromatic compounds, which processes proceed with desirable reaction rates, selectivity, and activity stability.

SUMMARY OF THE INVENTION

Embodiments of the invention are directed to hydrogenation catalysts, and hydrogenation processes using these catalysts, having particular characteristics, in terms of the amount and type of metal hydrogenation component (which may comprise one or more catalytically active constituents), as well as the support or substrate. The catalyst compositions provide advantageous performance characteristics, including conversion, selectivity, and activity stability, as demanded in industrial hydrogenation and selective hydrogenation applications (e.g., the hydrogenation of benzene to cyclohexane or the selective hydrogenation of dienes to mono-olefins). Aspects of the invention relate to the discovery of catalysts exhibiting such performance characteristics using a low content of the metal hydrogenation component, which includes a noble metal and a lanthanide element, deposited on a substantially non-porous substrate such as a glass-containing substrate. Without being bound by theory, it is believed that the observed hydrogenation performance benefits of catalysts described herein result from the ability of the lanthanide element to modify or stabilize the noble metal. More particular aspects of the invention relate to the discovery of synergistic effects obtained from combining europium with palladium, to provide the metal hydrogenation component in such catalysts, thereby achieving a high degree of hydrogenation activity and/or stability.

Particular embodiments of the invention are directed to catalysts comprising a noble metal and a lanthanide element deposited on a support comprising, consisting of, or consisting essentially of, a substantially non-porous substrate. Such substrates may be generally characterized as having a total surface area, as measured by $S.A._{N2\text{-}BET}$ or $S.A._{Kr\text{-}BET}$, between about 0.01 m$^2$/g and 10 m$^2$/g. These surface area measurements are described in greater detail below. In a preferred embodiment, the noble metal is palladium and the lanthanide element is europium. Each of these elements may be used judiciously, such that each may advantageously be present in amounts of less than about 1000 parts per million (ppm) by weight, based on the catalyst weight. Representative substantially non-porous substrates include various types of glass, and especially in the form of fibers (or fiberglass), such as AR-glasses, rare earth sodium silicate glasses, silico boroaluminate glasses, E-glasses, boron-free E-glasses, S-glasses, R-glasses, rare earth-silicate glasses, Ba—Ti-silicate glasses, nitrided glasses, A-glasses, C-glasses and CC-glasses and mixtures thereof.

Other particular embodiments of the invention are directed to processes for hydrogenating, or selectively hydrogenating, a feedstock comprising a compound having a hydrogenatable site. The processes comprise contacting the feedstock with hydrogen in the presence of a hydrogenation catalyst as described above. Representative compounds having at least one hydrogenatable site, or site of unsaturation, include heteroatom-substituted hydrocarbons having, as a hydrogenatable site, a carbon-heteroatom bond, wherein the heteroatom is selected from the group consisting of O, N, S. Other compounds include hydrocarbons, such as olefins, alkynes, or aromatics, having from 2 to 20 carbon atoms and at least one carbon-carbon double bond (e.g., at least two carbon-carbon double bonds such as in the case of a diene) or at least one carbon-carbon triple bond. Particular types of compounds which may be contained in the feedstock and hydrogenated, or selectively hydrogenated, include alkynes (e.g., acetylene), dienes (e.g., butadiene), and aromatic hydrocarbons (e.g., benzene).

In representative processes, the compound comprising the hydrogenatable site is converted to a corresponding compound, in which one or more hydrogenatable site(s) is/are saturated (e.g., cyclohexane), with a yield of at least about 90%. In the case of selective saturation processes, the hydrogenatable site that is saturated to this extent is relatively more reactive or susceptible to hydrogenation, compared to another type of hydrogenatable site that is relatively less reactive. The less reactive hydrogenatable site of a given compound can refer to the hydrogenatable site that survives after hydrogenation of the more reactive hydrogenatable site (e.g., the surviving carbon-carbon double bond of ethylene after selective hydrogenation of acetylene or the surviving carbon-carbon double bond of butene after selective hydrogenation of butadiene). Therefore, these more and less reactive hydrogenatable sites may be present in the same compound (e.g., a diene) of the feedstock or otherwise present in different compounds (e.g., an alkyne and an olefin) of the feedstock.

Further particular embodiments of the invention are directed to methods for preparing the hydrogenation catalyst as described above. The methods comprise (a) contacting fibers of the substantially non-porous substrate with an acid (e.g., an inorganic acid such as nitric acid, hydrochloric acid, or sulfuric acid) to provide an acid-leached substrate, (b) ion exchanging the acid-leached substrate with one or more ion exchange solutions comprising ions of the noble metal (e.g., palladium) and ions of the lanthanide element (e.g., europium) to provide an ion-exchanged substrate having the noble metal and lanthanide element deposited thereon; and (c) reducing the ion-exchanged substrate in the presence of hydrogen under reducing conditions, to provide the catalyst. In a preferred embodiment, ion exchanging the acid-leached substrate is performed with a single ion exchange solution comprising both palladium ions and europium ions (e.g., with the palladium ions being present as either palladium tetraamine nitrate or palladium tetraamine hydroxide, and the europium ions being present as europium nitrate). Preferably, the reducing conditions include a temperature from about 100° C. (212° F.) to about 400° C. (752° F.) and flowing hydrogen.

These and other embodiments, and their associated advantages, relating to the present invention are apparent from the following Detailed Description.

DETAILED DESCRIPTION

Figure 1:
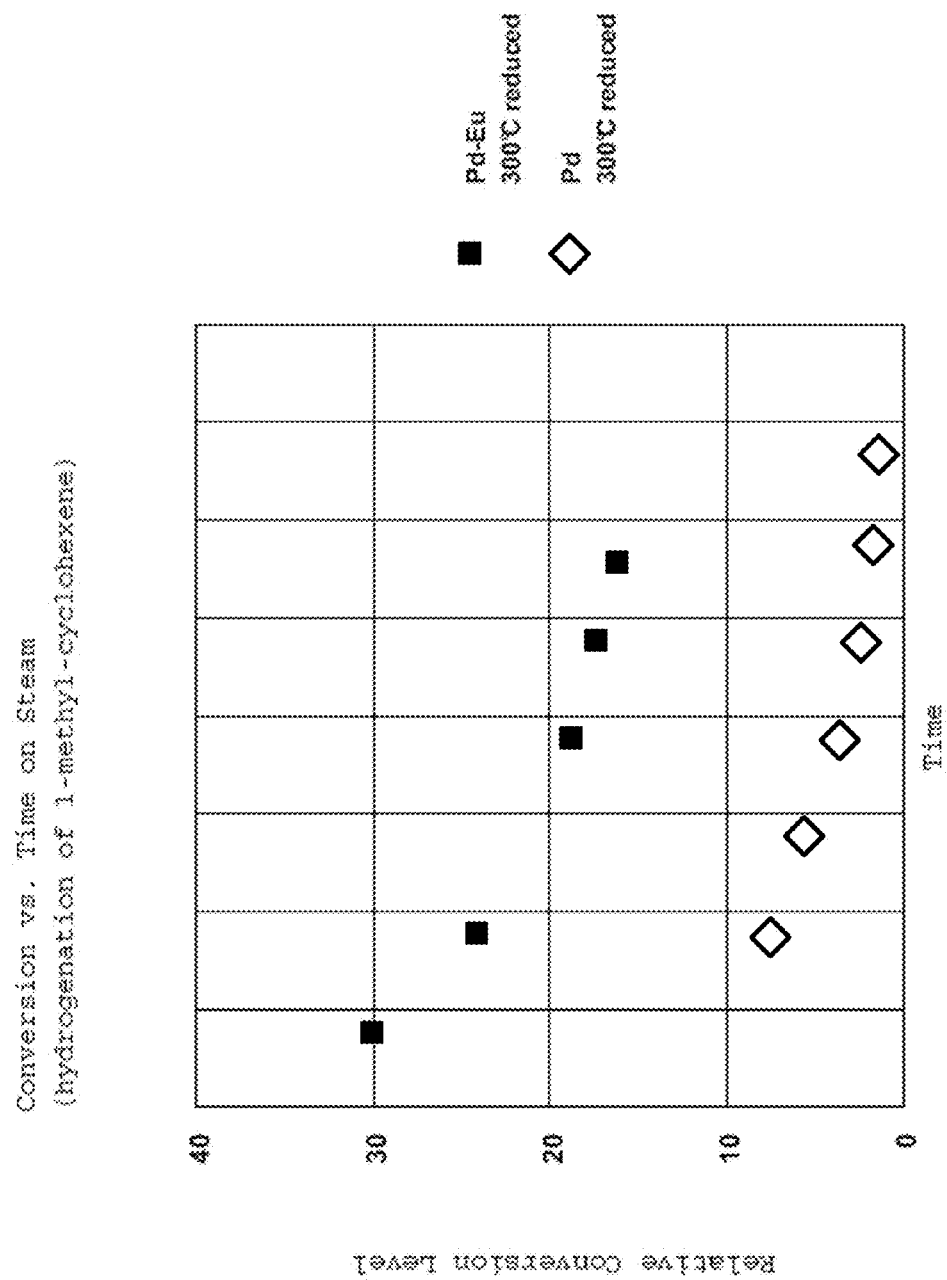
FIG. 1 is a graph showing conversion as a function of time on stream, for the hydrogenation of 1-methyl-cyclohexene to 1-methyl-cyclohexane, in the presence of noble metal/lanthanide element catalysts as described herein.

As discussed above, aspects of the invention relate to catalysts comprising a noble metal and a lanthanide element deposited on a support comprising a substantially non-porous substrate, hydrogenation processes using these catalysts, and methods of making these catalysts. In general, the substantially non-porous substrate may be present in the support in an amount of up to 100%, in which case the support would consist of the substantially non-porous substrate. According to other embodiments, for example when a forming medium is present in the support, the substantially non-porous substrate may be present in the support in an amount ranging from about 10% to about 99% by weight, and often from about 50% to about 90% by weight. Representative forming media include boehmite, hydrous titania and TiO$_2$, hydrous zirconia and ZrO$_2$, gamma alumina, alpha alumina, silica, clays, natural and synthetic polymeric fibers, polymeric resins, and solvent- and water-soluble polymers.

The characterization of a substrate as being substantially non-porous does not preclude the presence, in the substrate, of materially insignificant amounts of micro-, meso- and/or macro-pore volume, which do not adversely affect the performance of the hydrogenation catalyst. Since micropore volume in a material is often difficult to detect, surface area measurements using differing analytical techniques may be relevant in the determination of whether a given substrate is substantially non-porous. One technique for determining the extent of micro-, meso- and/or macro-pore volume is based on thermal adsorption/desorption. In the case of relatively high surface area measurements, namely at least 3 m$^2$/g, N$_2$ BET (based on thermal N$_2$ adsorption/desorption) according to ASTM D3663-03, ("$S.A._{N2\text{-}BET}$") is used. In the case of relatively low surface area measurements, namely less than 3 m$^2$/g, Kr BET (based on thermal Kr adsorption/desorption) according to ASTM D4780-95 ("$S.A._{Kr\text{-}BET}$") is used.

Another technique for determining the extent of micro-, meso- and/or macro-pore volume is based on sodium chemisorption. Sodium-chemisorption surface area ("S.A.$_{Na}$") can be expressed as a change vs. time in NaOH titrant, using the analytical method described by R. Iler in CHEMISTRY OF SILICA, John Wiley & Sons (1979) at p. 203 and 353, which is characterized as the S.A.$_{Na}$ rate of change ("SARC$_{Na}$"). Further details regarding the measurement of S.A.$_{Na}$, using an empirical titration procedure, are found in US 2009/0275788, hereby incorporated by reference with respect to this measurement. SARC$_{Na}$ refers to the ratio of two volumes of NaOH titrant. The denominator of this ratio is the volume of NaOH titration solution used initially, to titrate at time zero, $t_0$, a substrate slurry mixture containing 1.5 g of the substrate in 3.4M NaCl solution from pH 4 to pH 9 at about 25° C. Prior to this initial titration, the aqueous slurry mixture is adjusted to pH 4, using either a small amount of an acid (e.g., HCl) or a base (e.g., NaOH), as needed. The cumulative volume of NaOH titration solution used at three 5-minute intervals, to maintain the substrate slurry mixture at pH 9 over 15 minutes, is $V_{total}-V_i$ (i.e., $V_{5\,to\,15}$), which is the numerator of the ratio SARC$_{Na}$. Therefore, if $V_{total}-V_i$ is less than or equal to $0.5V_i$, the value of SARC$_{Na}$ is less than or equal to 0.5.

Representative substantially non-porous substrates have a surface area, as measured by S.A.$_{N2\text{-}BET}$ or S.A.$_{Kr\text{-}BET}$, in the range from 0.01 m$^2$/g to 10 m$^2$/g. According to preferred embodiments, in addition to meeting this surface area, representative substantially non-porous substrates have a SARC$_{Na}$ of 0.5 or less. These preferred substrates with an SARC$_{Na}$≤0.5 will be substantially non-porous as defined herein, provided that the S.A.$_{N2\text{-}BET}$ or S.A.$_{Kr\text{-}BET}$ is also in a range from about 0.01 m$^2$/g to about 10 m$^2$/g. When these surface area parameters are satisfied, to the extent the substrate has any micropore, mesopore and/or macropore volume, this volume has insufficient pore concentration, distribution and/or type to adversely affect the hydrogenation performance of the resulting catalyst composition.

Representative substantially non-porous substrates are glass compositions, and preferably fiberglass compositions. Examples of glass types for use as substantially non-porous substrates include E-glasses, boron-free E-glasses, S-glasses, R-glasses, AR-glasses, rare earth-silicate glasses, Ba—Ti-silicate glasses, nitrided glasses such as Si—Al—O—N glasses, A-glasses, C-glasses and CC-glasses. Each of these glass types are known in the art, particularly with respect to the compositions they embrace. AR-glass, for example, generally contains basic oxide type glass network modifiers in substantial amounts, often 10% by weight or more, of the total glass composition. These basic oxide network modifiers include oxides of Zr, Hf, Al, lanthanides, and actinides, as well as alkaline earth oxides (group 2), alkali oxides (group 1), and the like. Glasses containing oxides of Zr, Hf, Al, and/or lanthanides, and/or alkaline earth oxides, and/or alkaline oxides are preferred. Glasses containing oxides of Zr are particularly preferred.

A-type glass generally contains either acidic or basic oxide type glass network modifiers, including oxides of Zn, Mg, Ca, Al, B, Ti, Fe, Na, and/or K. In the case of basic network modifiers, the amount incorporated is generally less than 12% by weight. Glasses containing oxides of Mg, Ca, Al, Zn, Na, and/or K are preferred.

E-type glass, which includes non-leached E-type glass, generally contains either acidic or basic oxide type glass network modifiers, including oxides of Zn, Mg, Ca, Al, B, Ti, Fe, Na, and/or K. In the case of basic network modifiers, the amount incorporated in non-leached E-type glasses tends to be less than 20% by weight. Non-leached E-glasses containing Mg, Ca, Al, Zn, Na, and/or K are preferred.

The substantially non-porous substrate may be present in the catalyst composition in a variety of forms. Examples include fibers (i.e., in the form of fibers such as fiberglass), fibrillated fibers, cylindrical particles (e.g., pellets), spherical particles (e.g., spheres), elliptical particles (e.g., ellipsoids), flat particles (e.g., flakes), irregular fractured particles, spiral or helical particles, extrudates, rings, saddles, cartridges, membranes, spiral bound membranes, filters or a combination thereof. When in the fiber form, the substrate may be, more particularly, a woven composite, a nonwoven composite (e.g., having unidirectionally oriented fibers), a mesh fabric, a fiber tow, a chopped fiber material (e.g., a felted material), or a combination thereof. Preferably, when glasses such as A-glasses and E-glasses are used as the substantially non-porous substrate, they are in the form of fibers. Representative fibers have diameters in the range from about 100 nanometers (nm) to about 1 micron (μm), and often from about 200 nm to about 800 nm.

The surface of the substrate, and particularly a glass substrate, may be activated by an acid leach treatment involving contacting the substrate, for example in the form of fibers, with an acid suitable for removing a desired ionic species in a substantially heterogeneous manner across the substrate surface. This removal is generally achieved without significant erosion of the substrate network and/or significant creation of micropore structure, either on or below the surface. The acid may be organic or inorganic, with inorganic acids being preferred. Representative acids include nitric acid, phosphoric acid, sulfuric acid, hydrochloric acid, acetic acid, perchloric acid, hydrobromic acid, chlorosulfonic acid, trifluoroacetic acid and mixtures thereof.

An appropriate strength of an acid solution for use in an acid leach treatment depends on the properties of the substrate, for example its affinity for ion(s) to be removed (e.g., from a glass network), its strength after certain network ions are removed, and other properties. The strength or concentration of an acid solution used in an acid leach treatment ranges generally from about 0.5% to about 50%, typically from about 1% to about 25%, and often from about 2.5% to about 10%, by weight.

Other acid leach conditions, including heat treatment conditions (e.g., acid leach heating temperature, acid leach heating time and acid leach mixing conditions), for the acid leach treatment are selected in view of the type and strength of the acid used and the properties of the substrate. Representative acid leach heating temperatures are generally from about 20° C. (68° F.) to about 200° C. (392° F.), typically from about 40° C. (104° F.) to about 120° C. (248° F.) and often from about 60° C. (140° F.) to about 95° C. (203° F.). Representative acid leach heating times (i.e., the duration of heating when the desired heating temperature, of the substrate and the acid, is achieved) are generally from about 15 minutes to about 48 hours and typically from about 30 minutes to about 12 hours. Representative acid leach mixing conditions (i.e., during the ion exchange heating time) for the substrate and the acid include continuous or intermittent mixing. Mixing may be performed by hand (e.g., by shaking) or may be automated (e.g., tumbling, rolling, shaking, etc.).

Following the acid leach treatment, the acid-leached substrate is preferably isolated from the acid by any suitable method, including filtering, centrifuging, decanting, etc. The acid-leached substrate is generally washed with one or more suitable rinsing liquids, such as deionized water and/or a suitable water-soluble organic solvent (e.g., methanol, ethanol, or acetone) and then dried at room temperature or elevated temperature (e.g., up to about 150° C. (302° F.)) for a period generally from 1 to 24 hours.

Overall, the acid leach conditions are generally based on a desired degree of modification of substrate surface properties. These properties include the isoelectric point (IEP), as well as the type and degree of surface charge, for example as needed to produce the surface active state desired for either subsequent treatment(s) of the substrate or for use in the catalyst. The significance of the IEP and representative ranges of IEP for the substantially non-porous substrate, as well as a number of other possible methods for modifying the surface properties of the substrate, including substrate surface activation, substrate contaminant removal treatment (e.g., by calcination), acid leach treatment (including treatment with chelating agents), back-ion exchange (BIX) treatment, and pH adjustment of both BIX treated and non-BIX treated substrates, are taught in detail in US 2009/027578, and these teachings are incorporated herein by reference.

The catalyst support, comprising the substantially non-porous substrate (e.g., glass fibers) after possible acid leaching (to provide an acid-leached substrate) and/or any other surface treatments as described above, is then contacted with catalytically active constituents, namely a noble metal (e.g., ruthenium, rhodium, palladium, silver, osmium, iridium, platinum, and/or gold) and a lanthanide element (e.g., lanthanum, cerium, neodymium, europium, and/or ytterbium). Preferably, these catalytically active constituents are present in solution, such as an aqueous solution and preferably an ion exchange solution. Representative embodiments of the invention therefore comprise ion exchanging the substrate, including an acid-leached substrate, or a substrate that has been subjected to any other surface treatment, or combination of treatments described herein, with one or more ion exchange solutions comprising ions of the noble metal and ions of the lanthanide element, to provide an ion-exchanged substrate having the noble metal and lanthanide element deposited thereon.

Any salt solutions containing ions of both of the catalytically active constituents, or otherwise separate solutions containing ions of different catalytically active constituents, may be used for ion exchange. Ions of the catalytically active constituents are generally considered precursors of these constituents pending, for example, adjustment of their charge by reduction or oxidation, or otherwise pending any other type of post deposition treatment. However, it is also possible that ions of the catalytically active constituent(s) in ion exchange solution(s) may be catalytically effective in their precursor state, as deposited on the substantially non-porous substrate. Suitable catalytically active constituent ions are capable of displacing ions on the substantially non-porous substrate, either after acid leaching or other surface treatment as described herein. Otherwise, the catalytically active constituent ions have a charge affinity for this substrate. Suitable ion exchange solutions are generally salt solutions comprising cations of the catalytically active constituent(s) and possibly other cations (e.g., ammonium ions), as well as charge-balancing counterions (e.g., anions such as nitrate, hydroxide, halides, oxyanions, etc.). Representative ion exchange solutions for depositing (through ion exchange) the noble metal and the lanthanide element onto the substantially non-porous substrate (e.g., following an acid leach treatment) therefore include, solutions comprising metal salts of the noble metal and/or the lanthanide element (and preferably comprising metal salts of both of these catalytically active constituents), for example palladium tetraamine nitrate [$Pd(NH_3)_4NO_3$], palladium tetraamine hydroxide [$Pd(NH_3)_4OH$], europium nitrate [$Eu(NO_3)_3$], ytterbium nitrate [$Yb(NO_3)_3$] etc.

Generally, the concentration of the salt solutions used for ion exchange treatment to deposit catalytically active constituents, such as a noble metal and a lanthanide element, onto the substantially non-porous substrate, depend on the type of substrate, the nature of any surface treatments to which the substrate was subjected, the affinity of the ions of the catalytically active constituents for the substrate surface, and the desired concentrations of the catalytically active constituents on the resulting hydrogenation catalyst. For most types of glass substrates, such as AR, A, or soda-lime glass, the concentration of representative salt solutions is such that the percent by weight (based on solution weight) of ions of a given catalytically active constituent (e.g., $Pd^{+2}$) is from about 1 ppm to about 1000 ppm.

Ions of different catalytic constituents (e.g., $Pd^{+2}$ ions of the noble metal and $Eu^{+3}$ ions of the lanthanide element) may be exchanged concurrently, for example in the case of a single ion exchange solution comprising ions of both noble metal(s) and lanthanide element(s), or otherwise they may be exchanged sequentially, for example in the case of separate ion exchange solutions comprising ions of the different catalytic constituents. In either case, the concentration(s) of the salt solution(s) is/are based on the relative loading desired for each type of catalytic constituent (or catalytic constituent precursor) on the substantially non-porous substrate, considering its relative affinity for each type catalytic constituent. For example, a relatively high affinity for a given catalytic constituent may warrant the use of an ion exchange solution having a relatively low concentration of that constituent, to achieve a given concentration of that constituent on the resulting catalyst. Overall, representative methods for preparing catalysts described herein therefore include ion exchanging the substantially non-porous substrate (e.g., an acid-leached substrate) with one or more ion-exchange solutions comprising ions of the noble metal and ions of the lanthanide element to provide an ion-exchanged substrate having the noble metal and lanthanide element deposited thereon.

As with the acid leach treatment described above, conditions for ion-exchanging also include heat treatment conditions (e.g., ion exchange heating temperature, ion exchange heating time, and ion exchange mixing conditions). These ion exchange heat treatment conditions are selected in view of the type and strength of the ion exchange solution used and the properties of the substrate. Representative ion exchange heating temperatures are generally from about 20° C. (68° F.) to about 200° C. (392° F.), typically from about 40° C. (104° F.) to about 120° C. (248° F.), and often from about 60° C. (140° F.) to about 110° C. (230° F.). Representative ion exchange heating times (i.e., the duration of heating when the desired heating temperature, of the ion exchange solution and the substrate, for example after the acid leach treatment, is achieved) are generally from about 15 minutes to about 48 hours and typically from about 30 minutes to about 12 hours. Representative ion exchange mixing conditions (i.e., during the ion exchange heating time) for the substrate and the ion exchange solution include continuous or intermittent mixing. Mixing may be performed by hand (e.g., by shaking) or may be automated (e.g., tumbling, rolling, shaking, etc.).

Following ion exchanging of the substrate, after initially having optionally undergone any of the surface methods for modifying the surface properties of the substrate (e.g., acid leaching), the resulting ion-exchanged substrate is preferably isolated from the ion exchange solution by any suitable method, including filtering, centrifuging, decanting, etc. The ion-exchanged substrate is generally washed with one or more suitable rinsing liquids, such as deionized water and/or a suitable water-soluble organic solvent (e.g., methanol, ethanol, or acetone) and then dried at room temperature or elevated temperature (e.g., up to about 150° C. (302° F.)) for a period generally from 1 to 24 hours.

Ion exchange heat treatment conditions are generally selected in view of the type and strength of the ion exchange solution used and the properties of the substrate (e.g., affinity of ion(s) to be exchanged into and out of a glass network, strength of the glass after certain network ions are removed, etc.) and the ion exchange heating time. Overall, the combination of the ion exchange solution strength and heat treatment conditions are suitable for integrating a sufficient amount and distribution of ions of the catalytic constituents on and/or in the substrate, as necessary for producing a catalyst composition effective for its intended use. As discussed above, preferred hydrogenation catalysts described herein, while being effective in catalyzing a desired hydrogenation or selective hydrogenation reaction, advantageously contain relatively small amounts of the catalytically active constituents, for example less than about 1% by weight (e.g., from about 10 ppm by weight to about 1% by weight) of one or more noble metals and less than about 1% by weight (e.g., from about 10 ppm by weight to about 1% by weight) of one or more lanthanide elements. These weight percentages are expressed based on the catalyst weight, including the substantially non-porous substrate, any forming media as described above, and/or any other catalyst component. According to particular embodiments, the catalyst may comprise less than about 1000 ppm by weight (e.g., from about 100 ppm by weight to about 1000 ppm by weight) of one or more noble metals and less than about 1000 ppm by weight (e.g., from about 100 ppm by weight to about 1000 ppm by weight) of one or more lanthanide elements.

Following ion exchange, the ion-exchanged substrate may be further treated to adjust properties of the substrate and/or the catalytic constituents, for example the oxidation state of the catalytic constituents. According to embodiments of the invention, such further treatments may be performed in a reactor designed to carry out a hydrogenation process (i.e., in situ in a hydrogenation reactor). Representative treatments following ion exchange include pH adjusting (to adjust surface charge), calcining, oxidizing, reducing, sulfiding, carbiding, nitriding, phosphiding, and boriding, as described in US 2009/0275788, the teachings of which, pertaining to such post ion exchange treatments, are incorporated herein by reference. A preferred treatment following ion exchange is a reduction or reducing step that lowers the oxidation state of one or more of the catalytic constituents. According to particular embodiments of the invention, methods for preparing catalysts described herein comprise reducing the ion-exchanged substrate in the presence of hydrogen under reducing conditions, to provide the catalyst.

Catalysts described herein, comprising a noble metal and a lanthanide element deposited on a support comprising a substantially non-porous substrate, are effective in hydrogenation processes, and more specifically in processes for hydrogenating a feedstock comprising a compound having a hydrogenatable site, such as a carbon-carbon double bond (e.g., in the case of alkenes), a carbon-carbon triple bond (e.g., in the case of alkynes), or a carbon-heteroatom bond, with typical heteroatoms being oxygen (O), nitrogen (N), or sulfur (S) (e.g., in the case of ketones, carboxylic acids, esters, aldehydes, imines, nitriles, thiones, thiocarboxylic acids, thioesters, or thioaldehydes). Representative processes comprise contacting a feedstock comprising a compound having a hydrogenatable site, with hydrogen in the presence of a catalyst as described herein.

Particular embodiments are directed to "selective" hydrogenation processes, which refer to a subset of hydrogenation processes that are also of significant industrial importance. In selective hydrogenation, one type of hydrogenatable site that is relatively more reactive or susceptible to saturation, is preferentially, or selectively, hydrogenated relative to another type of hydrogenatable site that is relatively less reactive or susceptible to hydrogenation. While both types of hydrogenatable sites are present in the feedstock to be hydrogenated, they may or may not be present in the same compound (i.e., they may be present in the same compound or in different compounds of the feedstock). For example, in the case of a feedstock comprising a mono-olefin such as an ethylene containing stream from a thermal ethane cracker, the selective hydrogenation of acetylene is highly desired. In this case, acetylene, as one compound of the feedstock, has a carbon-carbon triple bond that is a relatively more reactive hydrogenatable site compared to the carbon-carbon double bond of ethylene. Alternatively, a feedstock comprising a mono-olefin such as butene (e.g., as butene-1, butene-2, and/or isobutylene) may also comprise a di-olefin (or diene) such as butadiene, having two hydrogenatable sites in the same compound. In the desired, selective hydrogenation of butadiene, the relatively more reactive of these two hydrogenatable sites is selectively hydrogenated to yield additional butene. Further hydrogenation of this butene to butane is generally considered a non-selective hydrogenation, as butene, and not butane, is generally desired due to its higher value. The selective saturation of either acetylene or dienes in these examples eliminates reactive impurities that reduce the overall stability of the feed stream, while substantially maintaining the concentration of the desired mono-olefins.

The compound comprising a hydrogenatable site may be present in the feedstock in widely varying amounts, depending on the particular application. In the case of selective hydrogenation, a compound (e.g., acetylene) comprising a hydrogenatable site that is targeted for selective conversion via hydrogenation, may be present in only trace quantities, even though other compounds (e.g., ethylene) comprising hydrogenatable sites may be present in major amounts. The concentration of the compound comprising a hydrogenatable site refers to the concentration of that compound (e.g., acetylene or benzene) that is to be converted and the conversion of which is the main performance parameter used to evaluate the effectiveness of the hydrogenation or selective hydrogenation process. In some cases, therefore, the "compound comprising the hydrogenatable site" may comprise a class of compounds (e.g., dienes, which can include butadiene and pentadiene, or aromatic hydrocarbons, which can include benzene and methylbenzene) that are targeted for hydrogenation. According to representative embodiments, the compound having the hydrogenatable site is present in the feedstock in an amount from about 10 ppm by weight to about 99% by weight, but often from about 100 ppm by weight to about 10% by weight in the cases of selective hydrogenation. The feedstock, which is subjected to hydrogenation, by contacting with hydrogen in the presence of a hydrogenation catalyst described herein, may include a combination of process streams, one or more of which may comprise a compound having a hydrogenatable site. Such process streams include feed streams to processes downstream of the hydrogenation process (e.g., in which case the hydrogenation process serves as a pretreatment to the downstream process), intermediate transfer streams, recycle streams and/or discharge streams.

Compounds having hydrogenatable sites include hydrocarbons, which refer to compounds comprising primarily carbon (C) and hydrogen (H) atoms. A heteroatom-substituted hydrocarbon refers to a particular type of hydrocarbon having at least one atom other than C and H, which is namely a heteroatom, such that a carbon-heteroatom bond is present. This carbon-heteroatom bond of a heteroatom-substituted hydrocarbon, and especially in the case where the heteroatom is selected from the group consisting of O, N, and S, can serve as a hydrogenatable site, for example in the case of an unsaturated C=O, C=NH, or C=S bond. According to representative hydrogenation processes, in which feedstocks comprise hydrocarbons (e.g., heteroatom-substituted hydrocarbons) suitable for hydrogenation using catalysts described herein, exemplary hydrocarbons generally have from 2 to about 30 carbon atoms and exemplary heteroatom-substituted hydrocarbons generally have from 2 to about 30 carbon atoms and one or more heteroatoms selected from the group consisting of O, N, and S. Such hydrocarbons and heteroatom-substituted hydrocarbons have at least one hydrogenatable site that is susceptible to hydrogenation, under suitable hydrogenation conditions, to the desired product.

Different compounds having different types of hydrogenatable sites are possible. For example, polyenes, polyynes and cyclenes may have carbon-carbon double bond and/or carbon-carbon triple bond sites that are successive (successive double-double bonds only), conjugated, or separated by one or more saturated and/or substituted carbon atoms. Hydrocarbons and heteroatom-substituted hydrocarbons suitable for hydrogenation using hydrogenation catalysts described herein include, without limitation, alkenes, dienes, polyenes, alkynes, polyynes, cyclenes, aromatic hydrocarbons, unsaturated and saturated vegetable oils and other hydrogenatable oxygenates. Feedstocks suitable for hydrogenation can also have mixtures of alkenes or polyenes, aromatics or cyclenes, alkynes or polyynes and/or heteroatom-substituted hydrocarbons having at least one hydrogenatable site. Hydrogenatable oxygenates include ketones, aldehydes, carboxylic acids, quinones and other hydrocarbons having a carbon-oxygen bond as a hydrogenatable site, as well as optionally one or more other heteroatoms.

Preferred compounds having a hydrogenatable site and suitable for hydrogenation using the catalysts described herein have from 2 to 20 carbon atoms and at least one carbon-carbon double bond and/or at least one carbon-carbon triple bond. Olefinic hydrocarbons (e.g., normal olefins) having one carbon-carbon double bond and dienes having two carbon-carbon double bonds are non-limiting examples of such compounds. Other examples of such preferred compounds include normal polyenes and normal alkynes having 2 to 20 carbon atoms and aromatic hydrocarbons (whether substituted, unsubstituted, or present as fused ring structure) having 6 to 20 carbon atoms. Particular hydrocarbons of interest, as compounds having a hydrogenatable site, are normal olefins, normal polyenes, olefin-substituted aromatics, normal alkynes, olefinic-aldehydes and olefinic-ketones, with any of these hydrocarbons having 2 to 15 carbon atoms, as well as aromatic hydrocarbons having 6 to 8 carbon atoms.

Representative hydrogenation processes can be carried out using various types of reactors having one or more hydrogenation zones. The feedstock, comprising a compound having a hydrogenatable site, is sufficiently contacted in the presence of hydrogen, with the hydrogenation catalyst in a hydrogenation zone that is maintained under hydrogenation conditions, as described more fully below. The catalyst may be present as a fixed catalyst bed (either in a batchwise or continuous process) or a moving catalyst bed (e.g., as an axially downwardly-flowing bed or a fluidized bed). The catalyst bed in a hydrogenation zone may be entirely of one type of catalyst as described herein (e.g., with respect to the support, the catalytic constituent(s), and their concentrations), or may comprise two or more types of catalysts, with at least one of these types being a catalyst as described herein. When different types of catalysts are used in a hydrogenation zone, they may be blended in any suitable blending ratio or otherwise separated.

Generally, a fixed catalyst bed system is preferred, in which the feedstock and hydrogen are passed to a hydrogenation zone containing a fixed bed of the hydrogenation catalyst. The feedstock may be preheated to the desired reaction temperature, for example using a heater and/or by heat exchange with another process stream, such as the effluent exiting the hydrogenation zone. The hydrogenation zone may itself comprise one or more separate reaction zones, with heating and/or quenching therebetween, and/or the introduction of and/or the removal of process fluid therebetween, in order to ensure that the desired reaction temperature and/or reactant ratios is/are maintained on the input (upstream) side of each reaction zone. The feedstock may be contacted with the hydrogenation catalyst in an upward, downward or radial flow configuration. Radial flow of the feedstock through the catalyst bed is preferred. The feedstock may be in the liquid phase, a mixed vapor-liquid phase or the vapor phase when it contacts the catalyst. Preferably, it is in the vapor phase.

Hydrogenation conditions, under which the catalysts described herein can be used, can vary considerably and depend on the particular hydrogenation process. Representative hydrogenation conditions include a temperature (e.g., a hydrogenation zone temperature, measured as an average hydrogenation catalyst bed temperature) generally from about 0° C. (32° F.) to about 538° C. (1000° F.), an absolute pressure (e.g., a hydrogenation zone pressure) generally from about 100 kPa (14.5 psi) to about 13.8 MPa (2000 psi), and a liquid hourly space velocity (LHSV) (e.g., in a hydrogenation zone) generally from about 0.1 $hr^{-1}$ to about 20 $hr^{-1}$. As is understood in the art, the LHSV, or volumetric liquid flow rate over the catalyst bed divided by the bed volume, represents the number of equivalent resin bed volumes of feedstock processed every hour. LHSV is therefore related to the inverse of the feedstock residence time in the bed. The ratio of the moles of hydrogen to the moles of hydrocarbon compounds (hydrogen to hydrocarbon molar ratio) in the feedstock can also vary widely depending on the concentration of the compounds having the hydrogenatable site and the particular hydrogenation process. Representative hydrogen to hydrocarbon molar ratios at the inlet of a hydrogenation zone are generally from about 0.1:1 to about 50:1. Generally, hydrogen is present at the inlet of the hydrogenation zone in an amount ranging from about 50% to about 600% of the stoichiometric hydrogen requirement for complete hydrogenation of the hydrogenatable sites in the feedstock. The hydrogen may be present in one or more hydrogen-containing gas streams entering the hydrogenation zone, at varying purity (e.g., from about 10% to about 99% hydrogen by volume). Representative hydrogen-containing streams include make-up and recycle hydrogen streams. Pure hydrogen may also be introduced to the inlet of a hydrogenation reaction zone or as one of two or more hydrogen-containing gas streams introduced.

Performance of a given hydrogenation process may be based on the extent of conversion (to converted compounds) of the compound having the hydrogenatable site, the selectivity of the converted compounds to the desired compound(s) (e.g., the corresponding compound(s) in which the hydrogenatable site is at least partially saturated), and/or the yield (i.e., the product of conversion and selectivity) of the desired compound(s), expressed as a percentage of the theoretical yield (i.e., complete conversion with complete selectivity to the desired compound(s)). Preferably, the compound is converted to the desired compound (e.g., acetylene is converted to ethylene, butadiene is converted to butene, or benzene is converted to cyclohexane) with a yield generally of at least about 50% (e.g., from about 50% to about 99.9%), typically at least about 70% (e.g., from about 70% to about 99.5%), and often at least about 90% (e.g., in the range from about 90% to about 99%) of the theoretical yield. Conversion values and selectivity values are also normally within any of these ranges.

Overall, aspects of the invention are directed to hydrogenation catalysts comprising catalytic constituents of a noble metal and a lanthanide element deposited on a substantially non-porous substrate, the use of such catalysts in hydrogenation processes, and methods for preparing these catalysts using a combination of acid leach, ion exchanging, and reducing. In view of the present disclosure, it will be seen that several advantages may be achieved and other advantageous results may be obtained. Those having skill in the art will recognize the applicability of the methods disclosed herein to any of a number of catalysts and associated hydrogenation processes. Those having skill in the art, with the knowledge gained from the present disclosure, will recognize that various changes could be made in these catalysts and processes without departing from the scope of the present disclosure.

The following examples are set forth as representative of the present invention. These examples are not to be construed as limiting the scope of the invention as other equivalent embodiments will be apparent in view of the present disclosure and appended claims.

EXAMPLE 1

Hydrogenation Catalyst—Palladium and Europium on A-Glass Fibers

A sample of A-06F-glass fibers (Lauscha Fiber International, Lauscha, Germany) having a mean diameter of 500-600 nm was obtained. The as-received, non-calcined A-06F glass sample was subjected to an acid leach treatment. About 100 grams of the A-06F glass and 4 liters of 5.5 wt % nitric acid were each placed in a 4 liter wide-neck plastic container. The plastic container was placed in an air draft oven at 90° C. for 2 hrs and shaken briefly by hand every 30 minutes. After the acid leach treatment, the sample was filtered on a Buchner funnel with Whatman 541 paper and washed with about 12 liters of distilled water. Thereafter, the acid-leached sample was dried at 110° C. for 22 hrs.

The resulting acid-leached A-06F glass substrate was then subjected to ion exchanging. In this example, palladium tetra amine-nitrate [$Pd(NH_3)_4NO_3$] and hydrous Europium nitrate [$Eu(NO_3)_3 \times 5\ H_2O$] were used to prepare 1 liter of a bimetal solution of 0.0017 wt % palladium and 0.0017 wt % europium for ion exchanging (i.e., the ion exchange solution). A 16.85 gram portion of the acid-leached glass substrate was added to the ion exchange solution, and the pH of the resulting glass/ion exchange solution mixture was about 5. This mixture was then transferred to a 4 liter wide-neck plastic container, which was placed in an air draft oven at 100° C. for 4 hours. During this period of ion exchanging, the container was shaken briefly by hand every 30 minutes. The glass/ion exchange solution was filtered to collect the resulting ion-exchanged glass substrate on a Buchner funnel with Whatman 541 paper. The ion-exchanged glass substrate was washed with about 8 liters of distilled water and then dried at 110° C. for 22 hours.

The dried ion-exchanged substrate, having palladium and europium deposited thereon, was analyzed for its metals content by inductively coupled plasma atomic emission spectroscopy (ICP-AES) and found to contain about 0.071 wt % (710 wt-ppm) palladium and 0.023 wt % (230 wt-ppm) europium. The ion-exchanged substrate then underwent a reducing treatment in the presence of 2 liters/hour of hydrogen flow at 300° C. for 4 hours to provide a hydrogenation catalyst.

EXAMPLE 2

Hydrogenation Catalyst—Palladium and Ytterbium on A-Glass Fibers

A catalyst was prepared as described with respect to Example 1, except that ytterbium nitrate was used to prepare an ion exchange solution, in place of Europium nitrate, such that the solution contained 0.0017 wt % of both palladium and ytterbium. Upon analysis of the dried ion-exchanged glass substrate by ICP-AES, it was found to contain about 0.066 wt % palladium and 0.079 wt % ytterbium.

EXAMPLE 3

Hydrogenation Catalyst—Palladium on A-Glass Fibers

A sample of A-06F-glass fibers (Lauscha Fiber International, Lauscha, Germany) having a mean diameter of 500-600 nm was obtained. The as-received, non-calcined A-06F glass sample was subjected to an acid leach treatment. About 100 grams of the A-06F glass and 4 liters of 5.5 wt % nitric acid were each placed in a 4 liter wide-neck plastic container. The plastic container was placed in an air draft oven at 90° C. for 2 hrs and shaken briefly by hand every 30 minutes. After the acid leach treatment, the sample was filtered on a Buchner funnel with Whatman 541 paper and washed with about 12 liters of distilled water. Thereafter, the acid-leached sample was dried at 110° C. for 22 hrs.

The resulting acid-leached A-06F glass substrate was then subjected to ion exchanging. In this example, palladium tetra amine hydroxide [$Pd(NH_3)_4(OH)_2$] was used to prepare 3 liters of a solution of 0.0016 wt % palladium for ion exchanging (i.e., the ion exchange solution). A 48.73 gram portion of the acid-leached glass substrate was added to the ion exchange solution, and the pH of the resulting glass/ion exchange solution mixture was about 11. This mixture was then transferred to a 4 liter wide-neck plastic container, which was placed in an air draft oven at 50° C. for 2 hours. During this period of ion exchanging, the container was shaken briefly by hand every 30 minutes. The glass/ion exchange solution was filtered to collect the resulting ion-exchanged glass substrate on a Buchner funnel with Whatman 541 paper. The ion-exchanged glass substrate was washed with about 7.6 liters of a dilute $NH_4OH$ solution, prepared by mixing 10 grams of concentrated 29.8 wt % $NH_4OH$ solution with about 3.8 liters of distilled water, and then dried at 110° C. for 22 hours. The ion-exchanged substrate then underwent a reducing treatment in the presence of 2 liters/hour of hydrogen flow at 300° C. for 4 hours to provide a hydrogenation catalyst. The catalyst was analyzed for its metals content by ICP-AES and found to contain about 0.089 wt % (890 wt-ppm) palladium.

EXAMPLE 4

Hydrogenation of 1-Methyl-Cyclohexene

The hydrogenation catalysts prepared in Example 1 (Pd—Eu) and Example 3 (Pd) were tested in a microreactor screening study for their performance in the hydrogenation of 1-methyl-cyclohexene in the presence of cyclohexanone. In particular, a mixture of 50/50 w/w of 1-methyl-cyclohexene/cyclohexanone was passed over a fixed bed of each of these catalysts in separate experiments, with the same hydrogenation conditions of 100° C., 2.7 psig, and a hydrogen to hydrocarbon molar ratio of 26:1. The relative conversion level of the 1-methyl-cyclohexene as a function of time, for each of these catalysts is shown in FIG. 1. Although the total metals content for each of the catalysts was approximately the same, the results showed that the europium-palladium catalyst exhibited significantly higher activity than the catalyst with palladium alone.

EXAMPLE 5

Hydrogenation of 1-Heptene

Figure 2:
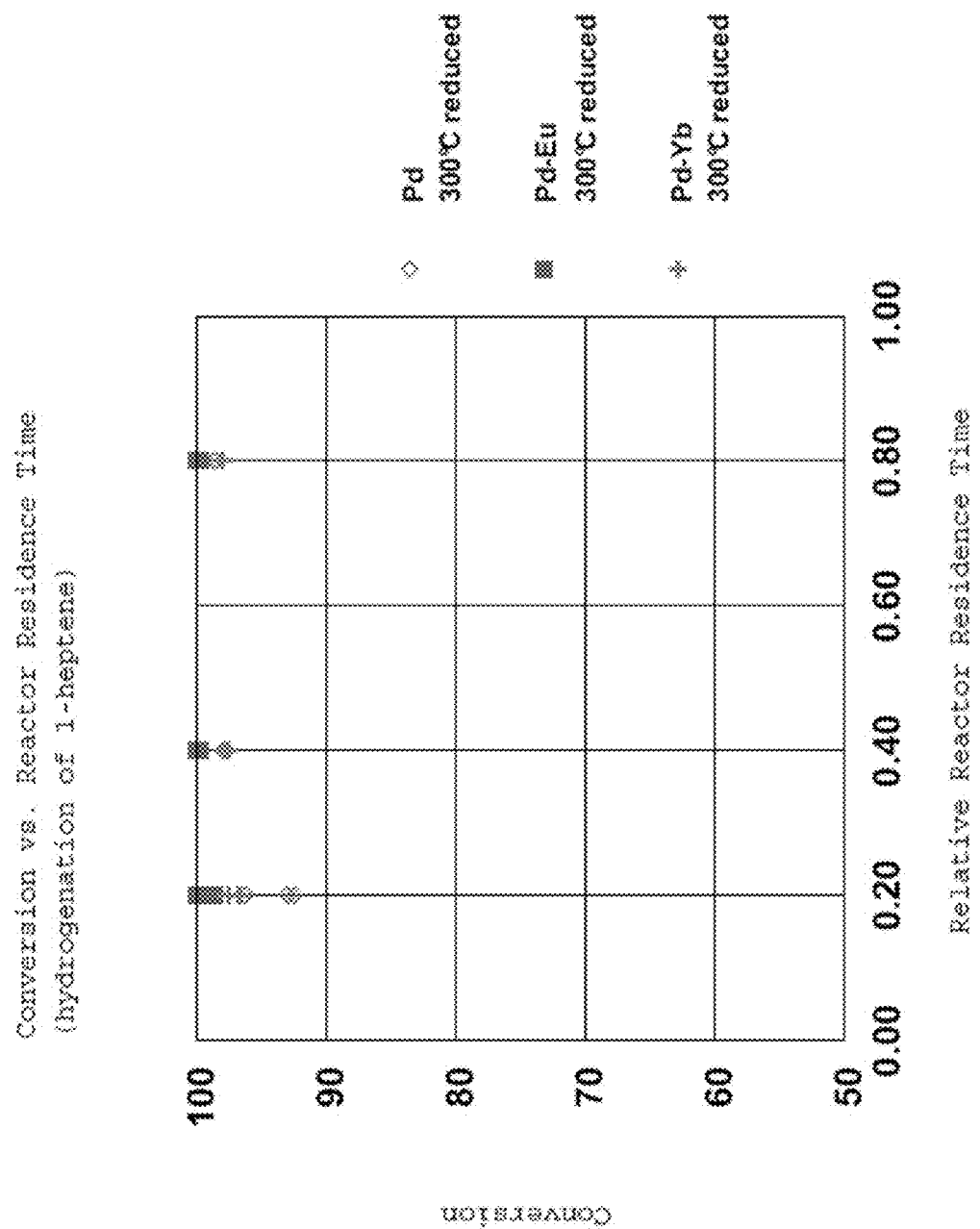
FIG. 2 is a graph showing conversion as a function of reactor residence time, for the hydrogenation of 1-heptene to heptane, in the presence of noble metal/lanthanide element catalysts as described herein.
Figure 3:
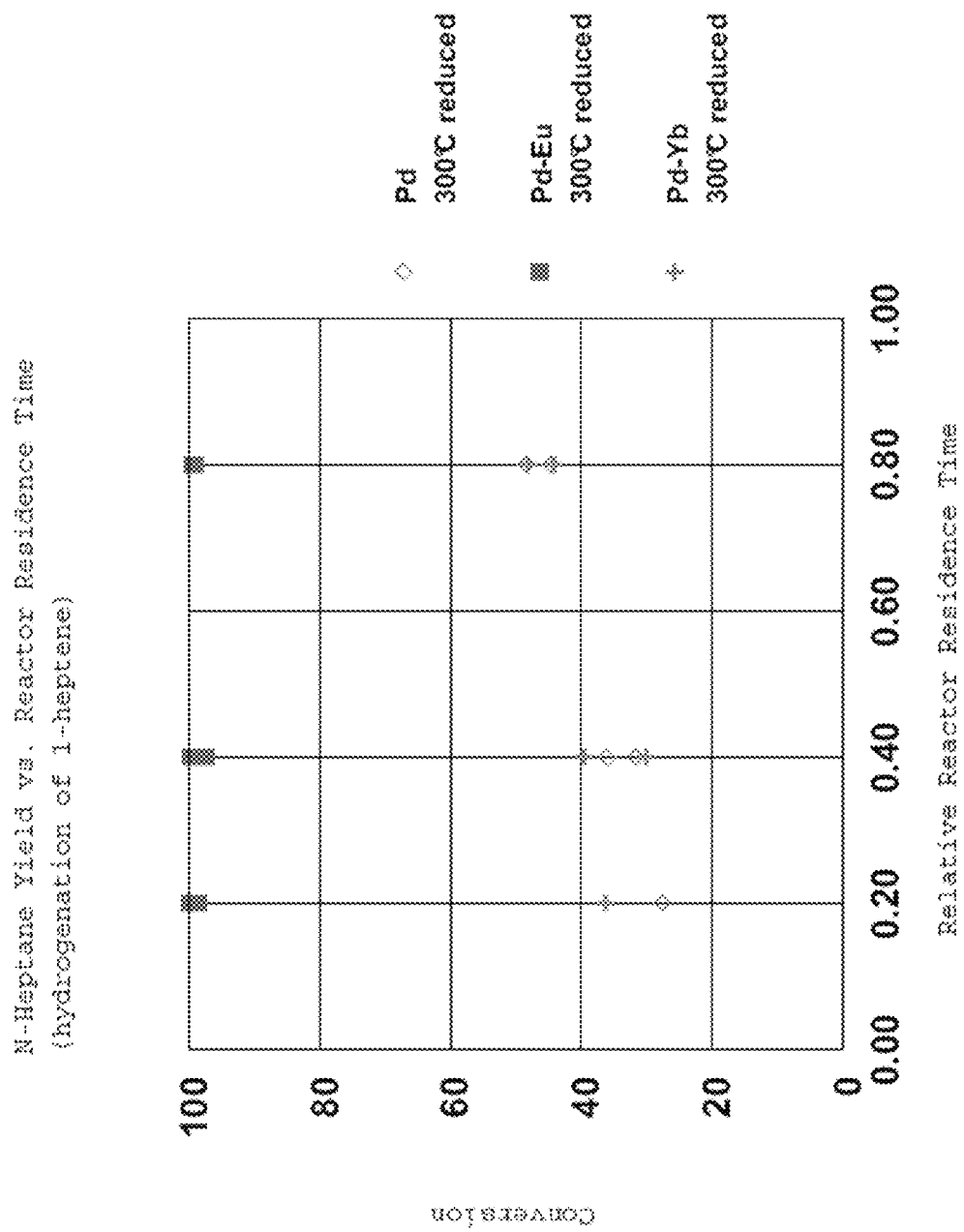
FIG. 3 is a graph showing n-heptane yield as a function of reactor residence time, for the hydrogenation of 1-heptene to heptane, in the presence of noble metal/lanthanide element catalysts as described herein.

The hydrogenation catalysts prepared in Example 1 (Pd—Eu), Example 2 (Pd—Yb), and Example 3 (Pd) were tested in a microreactor screening study for their performance in the hydrogenation of 1-heptene, which was passed over a fixed bed of each of these catalysts in separate experiments. Hydrogenation conditions of 200° C., 1 psig, and a hydrogen to hydrocarbon molar ratio of 50:1 were used in each experiment. The feedstock flow rate was variable, resulting in varying reactor residence times. FIG. 2 shows the conversion of 1-heptene as a function of reactor residence time, and FIG. 3 shows the yield of the hydrogenation product, n-heptane, as a function of reactor residence time. Again, the catalysts were active in catalyzing the desired hydrogenation of 1-heptene to n-heptane, but the Pd—Eu catalyst exhibited significantly improved performance relative to the catalysts comprising Pd—Yb and Pd alone, even at comparable metals loadings.

The invention claimed is:

1. A process for hydrogenating a feedstock comprising a compound having a carbon-carbon double bond, a carbon-carbon triple bond or a carbon-heteroatom bond, the process comprising contacting the feedstock with hydrogen in the presence of a catalyst comprising a noble metal and a lanthanide element deposited on a support comprising a substantially non-porous substrate having a surface area, as measured by $S.A._{N2\text{-}BET}$ or $S.A._{Kr\text{-}BET}$, from about 0.01 to about 10 $m^2/g$.

2. The process of claim 1 wherein the compound is a heteroatom-substituted hydrocarbon having, a carbon-heteroatom bond, wherein the heteroatom is selected from the group consisting of O, N, and S.

3. The process of claim 2 wherein the compound has from 2 to about 30 carbon atoms.

4. The process of claim 1 wherein the compound has from 2 to 20 carbon atoms and at least one carbon-carbon double bond or at least one carbon-carbon triple bond.

5. The process of claim 1 wherein the compound comprises at least two carbon-carbon double bonds.

6. The process of claim 1 wherein the compound is an aromatic hydrocarbon having from 6 to 20 carbon atoms.

7. The process of claim 1 wherein the compound is selected from the group consisting of alkenes, dienes, polyenes, alkynes, polyynes, cyclenes, aromatic hydrocarbons, unsaturated and saturated vegetable oils and other hydrogenatable oxygenates.

8. The process of claim 1 wherein the compound is selected from the group consisting of normal olefins, normal polyenes, olefin-substituted aromatics, normal alkynes, olefinic-alehydes and olefinic-ketones.

9. The process of claim 1 wherein the compound is selected from the group consisting of benzene, methylbenzene, 1-methyl-cyclohexane and 1-heptene.

10. The process of claim 1 wherein the compound is converted to a corresponding compound in which a hydrogenatable site is at least partially saturated, with a yield of at least about 90%.

11. The process of claim 1 wherein said compound is converted to a converted compound and wherein at least about 50% of said compound is converted to said converted compound.

12. The process of claim 11 wherein at least about 70% to about 99.5% of said compound is converted to said converted compound.

13. The process of claim 1 wherein the noble metal is palladium.

14. The process of claim 1 wherein the lanthanide element is europium.

15. The process of claim 1 wherein the substrate is a glass selected from the group consisting of AR-glasses, rare earth sodium silicate glasses, silico boroaluminate glasses, E-glasses, boron-free E-glasses, S-glasses, R-glasses, rare earth-silicate glasses, Ba—Ti-silicate glasses, nitrided glasses, A-glasses, C-glasses and CC-glasses and mixtures thereof.

16. The process of claim 15 wherein the glass is an A-glass, an E-glass, an AR-glass, or a mixture thereof.

17. The process of claim 15 wherein the glass is in a form selected from the group consisting of fibers, fibrillated fibers, cylindrical particles, spherical particles, elliptical particles, flat particles, irregular fractured particles, spiral or helical particles, extrudates, rings, saddles, cartridges, membranes, spiral bound membranes, filters and combinations thereof.

18. The process of claim 1 wherein the substrate is a glass containing oxides of Zr, Hf, Al, and/or lanthanides, and/or alkaline earth oxides, and/or alkaline oxides.

19. The process of claim 1 wherein said process is carried out in a fixed catalyst bed or a moving catalyst bed.

20. The process of claim 1 wherein the compound is converted to a corresponding compound in which a hydrogenatable site is at least partially saturated, with a yield of at least about 90%.

* * * * *